(12) United States Patent
Baid (10) Patent No.: US 9,199,063 B2
(45) Date of Patent: Dec. 1, 2015

(54) PROTECTOR COVER ASSEMBLY

(75) Inventor: Rishi Baid, New Delhi (IN)

(73) Assignee: POLY MEDICURE LTD., New Delhi (IN)

( * ) Notice: Subject to any disclaimer, the term of this patent is extended or adjusted under 35 U.S.C. 154(b) by 1234 days.

(21) Appl. No.: 12/438,717

(22) PCT Filed: Aug. 28, 2007

(86) PCT No.: PCT/IB2007/002472
§ 371 (c)(1),
(2), (4) Date: Nov. 19, 2009

(87) PCT Pub. No.: WO2008/026037
PCT Pub. Date: Mar. 6, 2008

(65) Prior Publication Data
US 2010/0082002 A1    Apr. 1, 2010

(30) Foreign Application Priority Data
Aug. 28, 2006   (IN) .......................... 1921/DEL/2006

(51) Int. Cl.
*A61M 5/32* (2006.01)
*A61M 25/06* (2006.01)
(52) U.S. Cl.
CPC ....... *A61M 25/0637* (2013.01); *A61M 25/0631* (2013.01); *A61M 5/3243* (2013.01); *A61M 5/3271* (2013.01); *A61M 2005/3247* (2013.01)
(58) Field of Classification Search
CPC ................. A61M 2005/3247; A61M 25/0631; A61M 25/0637; A61M 5/3243; A61M 5/3271
USPC ................ 604/192, 198, 164.08, 165.03, 177
See application file for complete search history.

(56) References Cited

U.S. PATENT DOCUMENTS

| 4,676,783 A | 6/1987 | Jagger et al. |
| 4,781,692 A | 11/1988 | Jagger et al. |
| 4,784,695 A | 11/1988 | Mito et al. |
| 5,085,639 A | 2/1992 | Ryan |
| 5,433,703 A | 7/1995 | Utterberg et al. |
| 5,562,631 A | 10/1996 | Bogert |

(Continued)

FOREIGN PATENT DOCUMENTS

| CN | 1468116 A | 1/2004 |
| CN | 1589165 A | 3/2005 |

(Continued)

OTHER PUBLICATIONS

English Translation and Office Action for related Russian Application No. 2011116510/14(024539) dated Feb. 20, 2015, 9 pages.

*Primary Examiner* — Kevin C Sirmons
*Assistant Examiner* — Deanna K Hall
(74) *Attorney, Agent, or Firm* — Kilpatrick Townsend & Stockton LLP (57) ABSTRACT

The invention relates to a needle protector assembly comprising a needle of a disposable medical device and a protective cover for the needle, wherein the needle is attached to a needle hub which can be moved relative to the protective cover between a position of use in which at least the tip of the needle is outside of the protective cover, and a retracted position iii which the needle is fully received in the protective cover, wherein the needle protector assembly further comprises a locking mechanism adapted to secure the needle hub inside the protective cover when the needle hub is in the retracted position.

19 Claims, 12 Drawing Sheets

(56) References Cited

U.S. PATENT DOCUMENTS

| | | |
|---|---|---|
| 5,683,365 A | 11/1997 | Brown et al. |
| 5,827,239 A | 10/1998 | Dillon et al. |
| 6,632,201 B1 * | 10/2003 | Mathias et al. ............... 604/263 |
| 7,303,545 B2 | 12/2007 | Sarstedt |
| 7,530,965 B2 | 5/2009 | Villa et al. |
| 2004/0225260 A1 | 11/2004 | Villa et al. |
| 2005/0049559 A1 | 3/2005 | Mathias |
| 2006/0276750 A1 | 12/2006 | Moriwaki et al. |
| 2007/0239118 A1 | 10/2007 | Ono et al. |

FOREIGN PATENT DOCUMENTS

| | | |
|---|---|---|
| DE | 101 56 587 A1 | 5/2003 |
| EP | 0 575 492 B1 | 11/1996 |
| EP | 1 323 442 A1 | 7/2003 |
| EP | 1 459 781 A1 | 9/2004 |
| RU | 2 169 585 C2 | 9/1998 |
| RU | 2 170 594 C1 | 10/1998 |
| RU | 2 276 611 C2 | 7/2002 |
| WO | WO 90/03196 A1 | 4/1990 |
| WO | WO 92/11885 A1 | 7/1992 |
| WO | WO 92/15351 A1 | 9/1992 |
| WO | WO 92/17229 A1 | 10/1992 |
| WO | WO 95/24232 A1 | 9/1995 |
| WO | WO 99/12594 A1 | 3/1999 |
| WO | WO 01/36025 A1 | 5/2001 |
| WO | WO 03/045491 A2 | 6/2003 |
| WO | WO 03/105928 A1 | 12/2003 |
| WO | WO 2004/089449 A1 | 10/2004 |

\* cited by examiner

PROTECTOR COVER ASSEMBLY

CROSS REFERENCE TO RELATED APPLICATIONS

This application is a National Stage of International Application No. PCT/IB2007/002472 filed Aug. 28, 2007 and which claims the benefit of India Patent Application No. 1921/DEL/2006, the disclosures of all applications being incorporated herein by reference.

The present invention relates to a needle protector assembly comprising a needle, for example of a disposable medical device, and a protective cover for the needle, wherein the needle is attached to a needle hub which can be moved relative to the protective cover between a position of use in which at least the tip of the needle is outside of the protective cover, and a retracted position in which the needle is fully received in the protective cover.

A needle protector assembly of this kind is generally known and helps to prevent accidental contact of a medical professional or any other person with the sharp tip of the needle after use of the disposable medical device. Such an accidental contact with a used needle can cause the transmission of a disease such as hepatitis, HIV, etc.

The increasing incidence of blood borne pathogens such as Human Immunodeficiency Virus (HIV), combined with Hepatitis B Virus (HBV) and Hepatitis C Virus (HCV), presents healthcare workers with an occupational hazard unprecedented in modern medicine. The risk of contracting HIV from a needle stick injury is approximately 1 in 100, but for those who contract HIV infection as a result of a needle stick injury the risk becomes 1 in 1. The risk of contracting the more contagious HBV as a result of a needle stick injury ranges from 1 in 6 to 1 in 20.

There are some other known blood borne pathogens which are transmitted via blood and bodily fluids. The presence of any of these pathogens in patients poses a risk to healthcare workers when invasive procedures are performed. Infectious diseases are now the third leading cause of death, behind heart disease and cancer, while ten years ago this was ranked fifth, signifying a growing need for safer medical devices.

As the population of infected individuals increases, more people will be treated by healthcare workers, which imposes further risks of disease transmission from patients to healthcare workers. Also, the use of disposable medical devices is increasing at approximately 10% per annum. Additionally, a remarkable number of patient to patient transmissions in the healthcare setting have been identified throughout the world. Early data suggests improper infection control techniques contribute directly to this increase: including improper use of medical devices having needles, multiple-dose medicine vials, and failure to change protective gloves and gear for each new patient.

Healthcare workers are increasingly at risk of disease transmission, and nurses perform the majority of invasive hypodermic procedures, such as injecting medicine, collecting blood and inserting indwelling intravenous (I.V.) catheters. Nurses and other healthcare personnel are routinely injured by the exposed, sharp lancet of the needle after use on a patient. The critical time where a percutaneous injury can occur is from the moment the needle is withdrawn from the patient, or I.V. port, to the time the contaminated needle is safely discarded.

Prior to the proliferation of HIV and serum hepatitis, a needle stick injury was considered a routine part of providing patient care. A needle stick injury now carries a life-threatening consequence and healthcare workers must live with this terror on a daily basis.

There is a requirement for a low-cost safety needle protector apparatus with a universal application.

It is an object of the invention to provide a needle protector assembly which provides reliable protection against accidental pricking by a needle, for example of a disposable medical device, and which is easy and inexpensive to manufacture.

This object is satisfied by a needle protector assembly having the features of claim 1.

A needle protector assembly of the invention comprises a needle, for example of a disposable medical device, and a protective cover for the needle, wherein the needle is attached to a needle hub which can be moved relative to the protective cover between a position of use in which at least the tip of the needle is outside of the protective cover, and a retracted position in which the needle is fully received in the protective cover. The needle protector assembly further comprises a locking mechanism adapted to secure the needle hub inside the protective cover when the needle hub is in the retracted position.

In other words, the invention proposes a needle protector assembly which locks the needle safely in the protective cover by an interlocking arrangement. The locking mechanism effectively prevents the needle from inadvertently protruding out of the protective cover. Thereby protection against accidental pricking by the needle is greatly increased. Consequently, the needle protector assembly of the invention ensures a safe disposal of the needle after its use.

It is to be noted that in the context of this invention the term of "needle" comprises any object having a sharp tip which can cause a percutaneous injury. Specifically, in this context the term of "needle" is understood to not only refer to a needle in the literal sense but also to a blade which has a sharp tip.

Examples of disposable medical devices in which the needle protector assembly can be used include not only devices which are used to collect blood from a patient or a donor or to give fluids to a patient, such as blood collection sets (PSV sets with luer adapters), blood collection bag needles, scalp vein sets, and fistula needles, but also scalpels with blades.

If the needle protector assembly is used in a blood collection set, then the needle hub may be a wing housing to which a PVC tube is connected, for the collection of blood drawn from a patient.

According to a preferred embodiment, the locking mechanism comprises at least one pair of first and second locking means engaging with each other when the needle hub is in the retracted position, wherein the first locking means is provided on the needle hub and the second locking means is provided on the protective cover.

At least two pairs of first and second locking means may be arranged on the same side of the needle protector assembly and spaced apart from one another seen in the axial direction of the needle, when the needle hub is in the retracted position.

Alternatively or additionally, at least one pair of first and second locking means may be arranged on a first side of the needle protector assembly, while at least one pair of first and second locking means may be arranged on a second side of the needle protector assembly opposite from the first side, when the needle hub is in the retracted position.

The needle protector assembly is particularly inexpensive to manufacture, if the first locking means is formed integrally with the needle hub. Alternatively, the first locking means may be formed on a separate element, for example a ring, which is attached to the needle hub.

Preferably, the first locking means defines a surface facing the needle tip, wherein at least a portion of the surface extends in a plane generally perpendicular to the needle. This makes a particularly effective interaction between the first and second locking means possible.

According to a preferred embodiment, the first locking means comprises a protrusion protruding from the needle hub.

For example, the first locking means may have a generally nose-like or ramp-like shape, with its radial dimension increasing towards the tip of the needle.

Preferably, the first locking means is formed such that a radial dimension of the locking means can be reduced against a restoring force. For example, the first locking means may be formed from a material having elastic properties. This may facilitate the movement of the needle hub into an interior passage of the protective cover.

The first locking means may be arranged in the region of a proximal end of the needle hub. This arrangement is particularly advantageous, when the needle hub is a wing housing.

Alternatively, the first locking means may be arranged in the region of a distal end of the needle hub. This arrangement is particularly advantageous, when the needle hub has a cuboid-like shape.

In the latter case, the first locking means may be formed from a shoulder of the needle hub facing the needle tip, wherein the shoulder preferably defines a surface of the needle hub facing the needle tip, such that at least a portion of the surface extends in a plane generally perpendicular to the needle.

According to a further embodiment, the second locking means comprises an opening, for example a slot, in the protective cover, which is adapted to receive the first locking means when the needle hub is in the retracted position. A second locking means in the form of an opening in the protective cover is particularly advantageous, when the first locking means is formed from a protrusion protruding from the needle hub and having elastic properties, such that it can engage in the opening if correctly positioned, thereby interlocking the needle hub and the protective cover.

According to an alternative embodiment, the second locking means comprises a locking tongue extending towards a proximal end of the protective cover and adapted to engage with the first locking means, when the needle hub is in the retracted position.

Preferably, the locking tongue has resilient properties and extends towards the interior of the protective cover, such that it is pushed outwards by the first locking means or by the needle hub as the needle hub is moved towards its retracted position, and snaps back behind the first locking means once the needle hub has adopted its retracted position. In the case of such a resilient locking tongue, a first locking means in the form of a protrusion protruding from the needle hub may have elastic properties; however, this is not compulsory.

The cost for the production of the needle protector assembly can be further decreased, if the locking tongue is integrally formed with the protective cover.

The protective cover preferably comprises guiding means for guiding the first locking means into engagement with the second locking means when the needle hub is moved towards its retracted position. The guiding means helps to ensure a secure interlocking between the first and second locking means, in particular, if the first locking means is a protrusion protruding from the needle hub and the second locking means is an opening for receiving the protrusion or a locking tongue for engaging behind the protrusion.

In order to achieve an even more reliable locking of the needle inside the protective cover, the locking mechanism preferably comprises a retaining element securing the interlocking of a pair of first and second locking means.

The retaining element may be formed on a side of the needle protector assembly opposite from the pair of first and second locking means. Thereby the retaining element helps to prevent the first locking means from becoming disengaged from the second locking means. Furthermore, the extension operates as a guide for the needle hub when the needle hub enters the internal passage of the flat portion of the protective cover. The retaining element may, for example, be an extension of the protective cover protruding from a proximal portion of the protective cover in a direction towards a distal end of the protective cover.

According to a further embodiment of the needle protector assembly, the protective cover comprises an elongate portion having the shape of one half of a tube cut at least approximately in half in the axial direction. A protective cover of this kind is particularly advantageous, if the needle hub is a wing housing, since the open shape of the elongate portion of the protective cover allows the wings of the wing housing to extend out of the protective cover while the needle attached to the wing housing is received inside the elongate portion, when the needle hub is moved towards its retracted position.

In addition, the protective cover preferably comprises a tubular portion in the region of a distal end of the protective cover and/or a flat portion in the region of a proximal end of the protective cover. The tubular portion prevents the needle from sticking sideways out of the protective cover, thereby further increasing the protective effect of the needle protector assembly.

The flat portion may comprise first and second parts defining an inner passage in which the needle hub is received when the needle hub is in the retracted position. In order to further reduce production costs, the first and second parts may be integrally formed and connected to one another by a film hinge.

In the assembled state, the first and second parts may be attached to one another by means of at least one of a latching mechanism, an adhesive and welding.

According to a further alternative embodiment of the needle protector assembly, substantially the entire length of the protective cover as seen in the axial direction is of generally tubular shape. This type of protective cover may, for example, be used when the needle hub does not have any wings and has, for example, the basic shape of a cuboid.

Preferred embodiments of the invention are described in the following description and in the accompanying drawings, wherein:

FIG. 10 is a cross-sectional view of a flat portion of the protective cover of the needle protector assembly of FIG. 1.

FIG. 11 is a perspective view of the top side of the protective cover of the needle protector assembly of FIG. 1.

FIGS. 12A, B are perspective views of the bottom side of the protective cover of the needle protector assembly of FIG. 1.

FIGS. 14A, B are perspective views of the protective cover of the needle protector assembly of FIG. 13.

FIGS. 15A, B are perspective views of the needle protector assembly of FIG. 13 with the needle received and locked in the protective cover.

In FIGS. 1 to 12 a needle protector assembly 10 according to a first embodiment of the invention is shown. The needle protector assembly 10 is part of a disposable medical device, for example a blood collection kit, having a hypodermic needle 12 and is provided to prevent accidental contact of a medical professional or any other person with the sharp tip 14 of the needle 12 after use of the disposable medical device.

Figure 1:
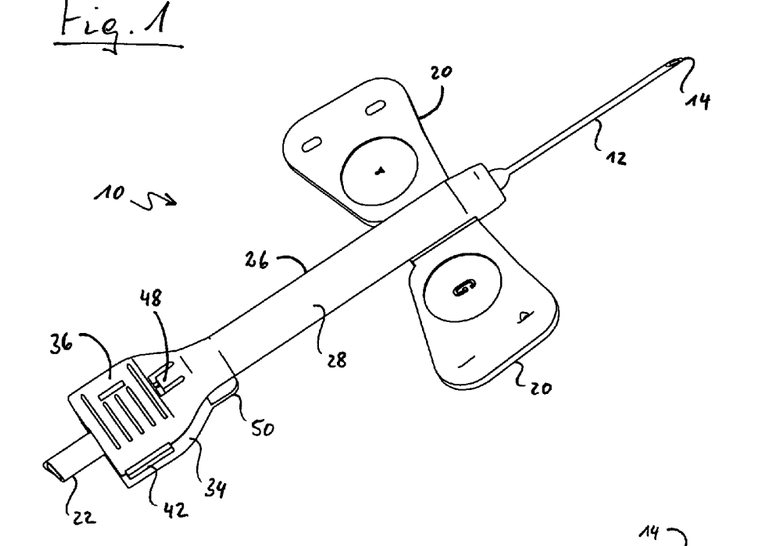
FIG. 1 is a perspective view of a top side of a needle protector assembly of the invention according to a first embodiment, wherein a needle protrudes beyond a protective cover.
Figure 2:
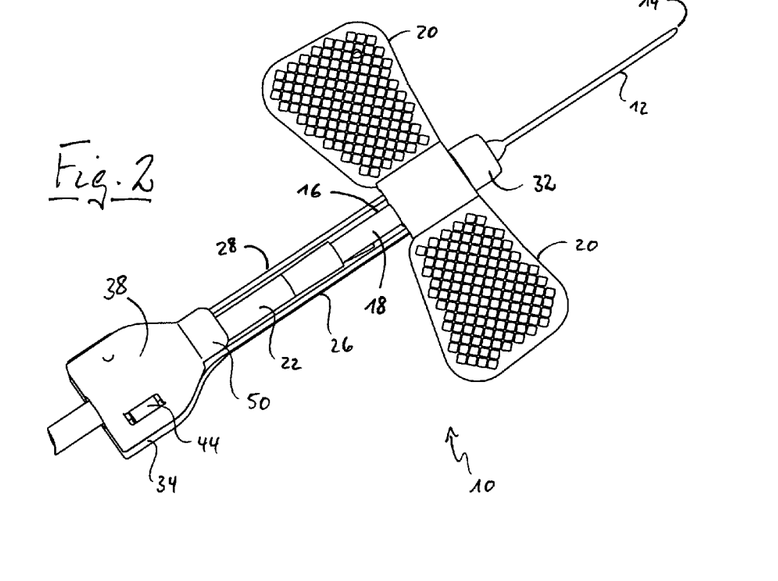
FIG. 2 is a perspective view of a bottom side of the needle protector assembly of FIG. 1 with the needle protruding beyond the protective cover.
Figures 3, 4:
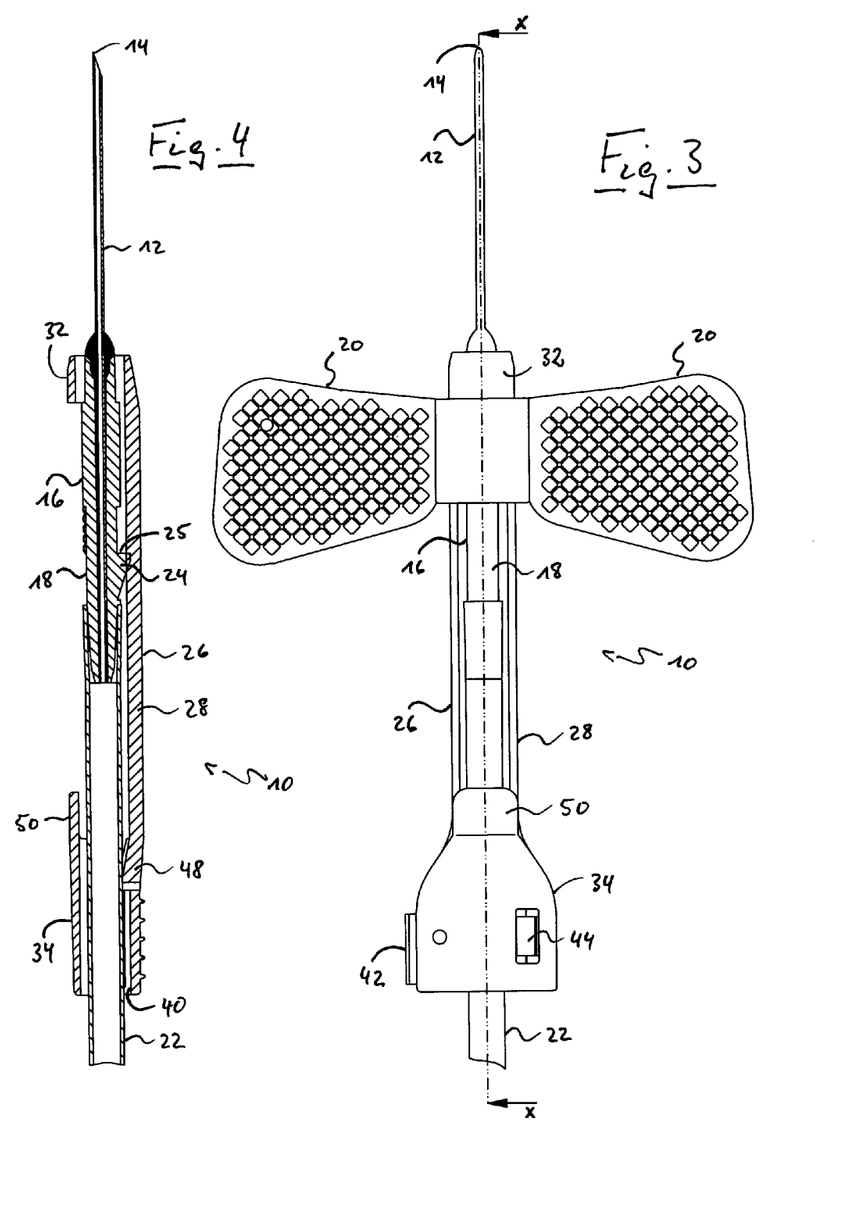
FIG. 3 is a plan view of the bottom side of the needle protector assembly of FIG. 1 with the needle protruding beyond the protective cover.
FIG. 4 is a cross-sectional view of the needle protector assembly of FIG. 1, taken along the line X-X in FIG. 3, with the needle protruding beyond the protective cover.
Figure 5:
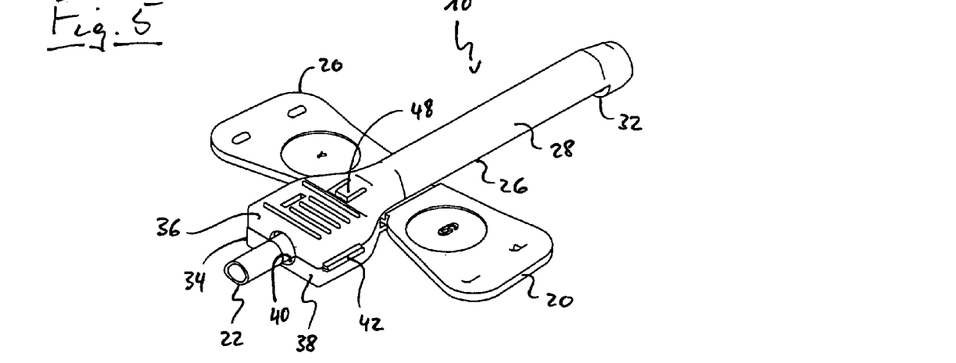
FIG. 5 is a perspective view of the top side of the needle protector assembly of FIG. 1 with the needle received and locked in the protective cover.
Figure 6A:
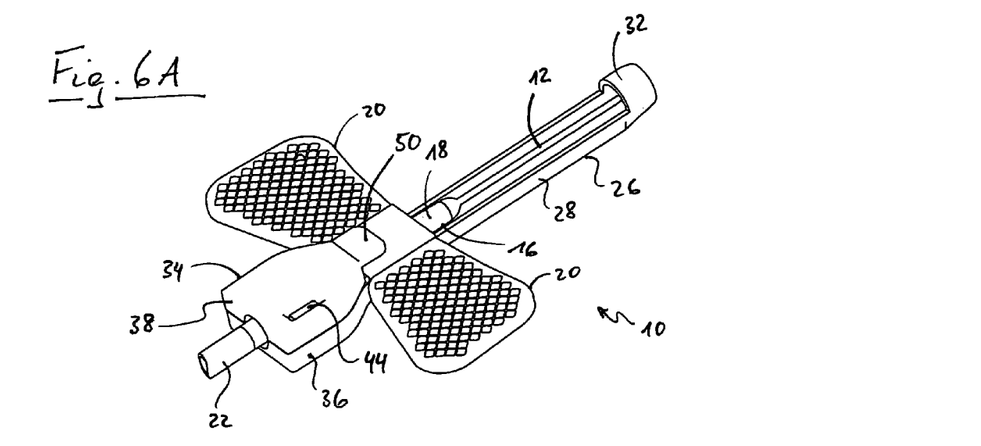
FIGS. 6A, B are perspective views of the bottom side of the needle protector assembly of FIG. 1 with the needle received and locked in the protective cover.
Figure 6B:
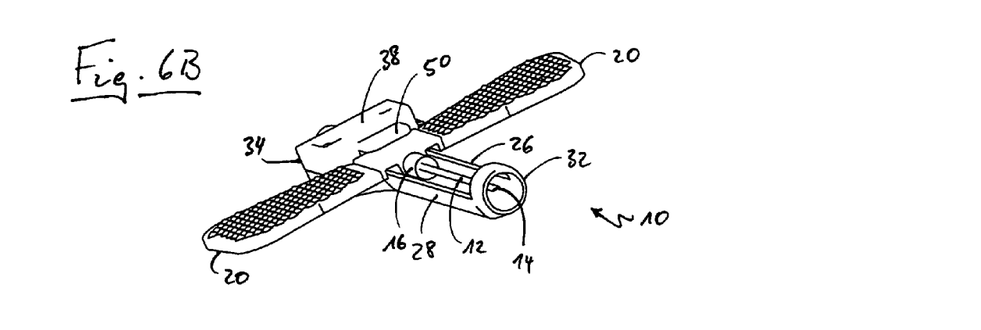
Figure 7:
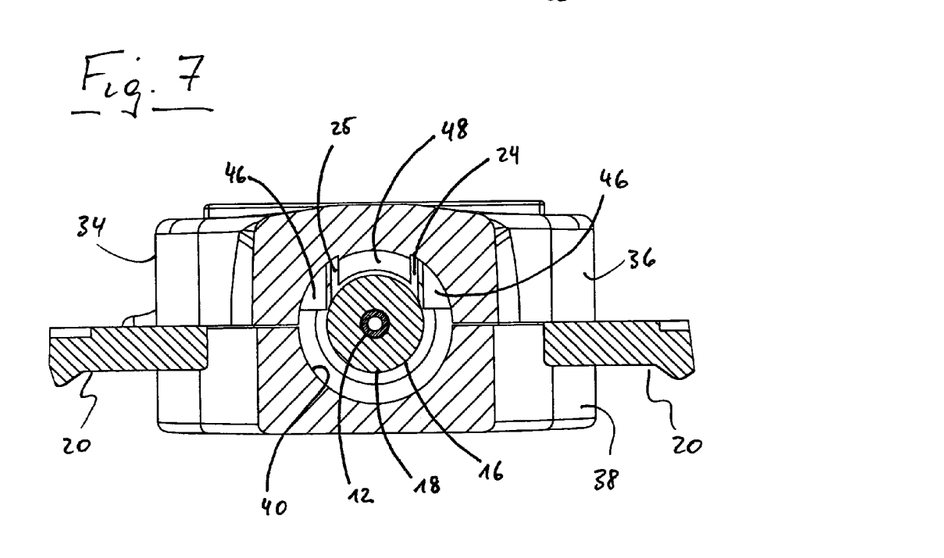
FIG. 7 is a cross-sectional view of the needle protector assembly of FIG. 1, taken along the line Y-Y in FIG. 7A, with the needle received and locked in the protective cover.
Figure 7A:
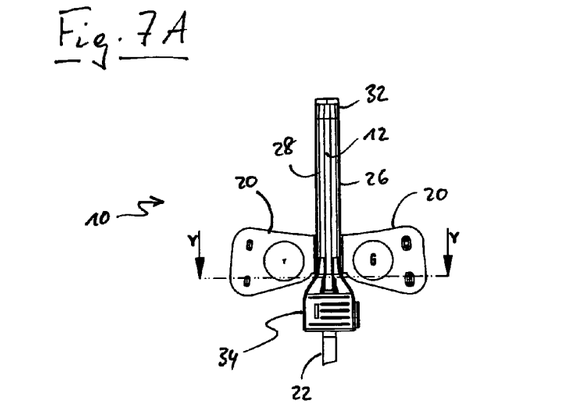

In this context, the end of the needle 12 having the sharp tip 14 is denoted the distal end, whereas the opposite end of the needle is denoted the proximal end. Likewise the orientation of parts of other structural elements facing towards the needle tip 14 will be referred to as distal, whereas the orientation of parts of these structural elements facing in the opposite direction will be referred to as proximal.

The needle 12 extends in an axial direction, thereby defining an axial direction for the needle protector assembly 10. A direction perpendicular to the axial direction is denoted as radial.

In the region of its proximal end the needle 12 is connected, for example glued, to a needle hub 16. The needle hub 16 of this embodiment is formed from a wing housing having a tubular main body 18 and two wings 20 which extend in opposite radial directions from the main body 18. The wings 20 can either be formed integrally with the main body 18, or they can be separate elements that are attached to the main body 18.

One end of a PVC tube 22 is attached, for example glued, to a proximal end portion of the needle hub 16. The other end of the PVC tube 22 may, for example, be connected to a blood collection bag (not shown) or any other component to facilitate flow of fluid, such as medicine or blood, to or from a patient or donor.

As can be seen from FIGS. 4, 7, 8 and 9, a locking protrusion 24 is arranged on a top side of the main body 18 of the needle hub 16 in a proximal region thereof. The locking protrusion 24 is integrally formed with the main body 18 and has a generally nose-like or ramp-like shape, with its radial dimension increasing towards the tip 14 of the needle 12. A distal surface 25 of the locking protrusion 24 facing the needle tip 14 extends in a plane generally perpendicular to the axial direction.

The needle protector assembly 10 further comprises a protective cover 26 in which the main body 18 of the needle hub 16 is slidably arranged. More specifically, the protective cover 26 includes an elongate portion 28 having the shape of one half of a tube cut at least approximately in half in the axial direction, thus defining a closed top side and an open bottom side of the elongate portion 28. The open bottom side of the elongate portion 28 allows the wings 20 of the needle hub 16 to extend sideways out of the protective cover 26 when the main body 18 of the needle hub 16 is received in the elongate portion 28.

Figures 10, 11, 12A, 12B:
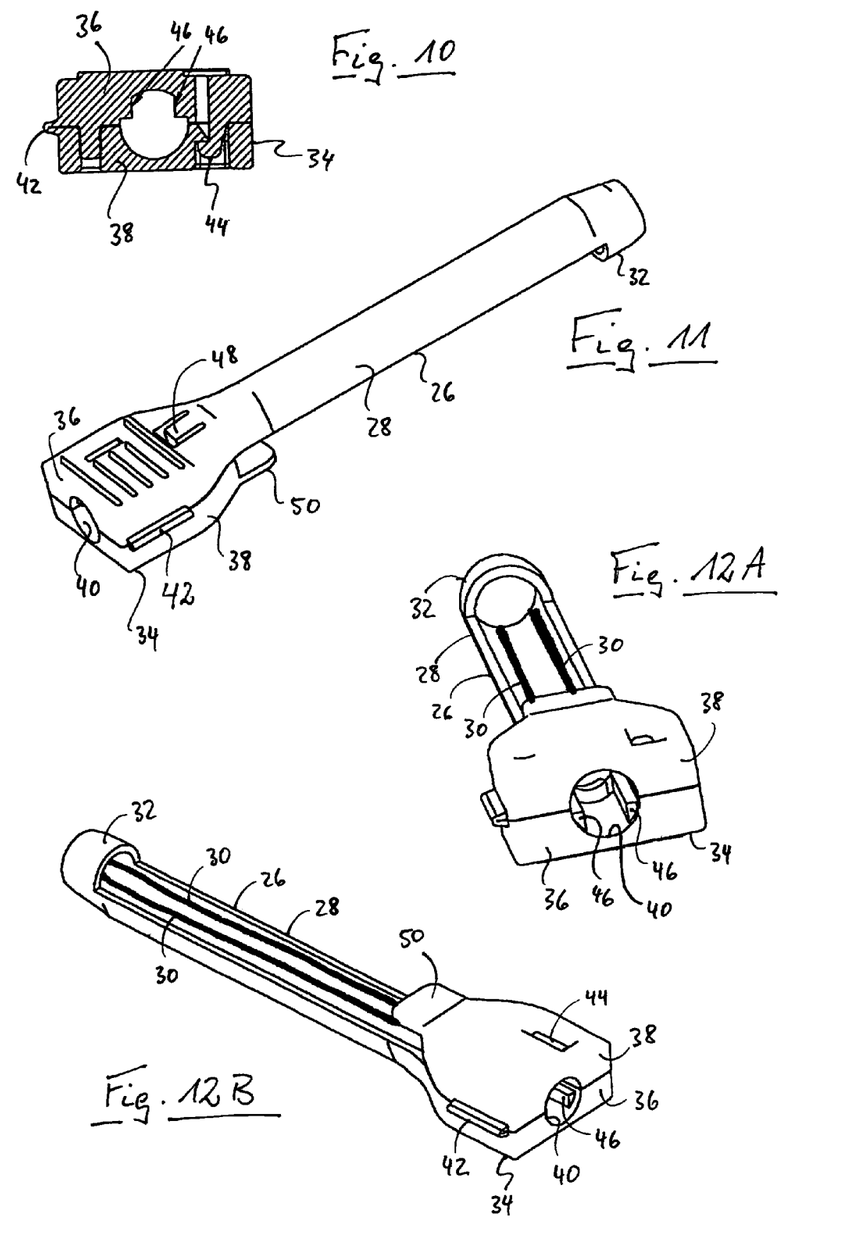

As is best seen in FIGS. 12A and 12B, guide rails 30 may be provided in the elongate portion 28, which extend in the axial direction and are adapted to control the orientation of the locking protrusion 24 when the needle hub 16 is moved along the elongate portion 28.

In the region of the distal end of the elongate portion 28, the protective cover 26 comprises a tubular portion 32 which prevents the needle 12 from coming sideways out of the protective cover 26.

In the region of the proximal end of the elongate portion 28, the protective cover 26 comprises a flat portion 34 which is formed from a top part 36 and a bottom part 38. The top and bottom parts 36, 38 together define an internal passage 40 through which the PVC tube 22 extends and in which the proximal end portion of the main body 18 of the needle hub 16 can be received.

As can be taken from FIGS. 10 to 12, the top and bottom parts 36, 38 are integrally formed and connected to one another by a film hinge 42. In addition, the top and bottom parts 36, 38 are locked to one another by a latching mechanism 44. Alternatively or additionally, they may be connected to each other by an adhesive or by a welding process.

Guide rails 46 are provided in the internal passage 40 of the flat portion 34, which are aligned with the guide rails 30 of the elongate portion 28 to control the orientation of the locking protrusion 24 when the needle hub 16 enters the flat portion 34.

A locking tongue 48 is provided in the top part 36 of the flat portion 34. The locking tongue 48 is integrally formed with the top part 36 and has resilient properties. The locking tongue 48 is aligned with the internal passage 40 and extends towards the proximal end of the protective cover 26 and into the internal passage 40 (FIGS. 4, 8, 9A and 9B).

Figure 8:
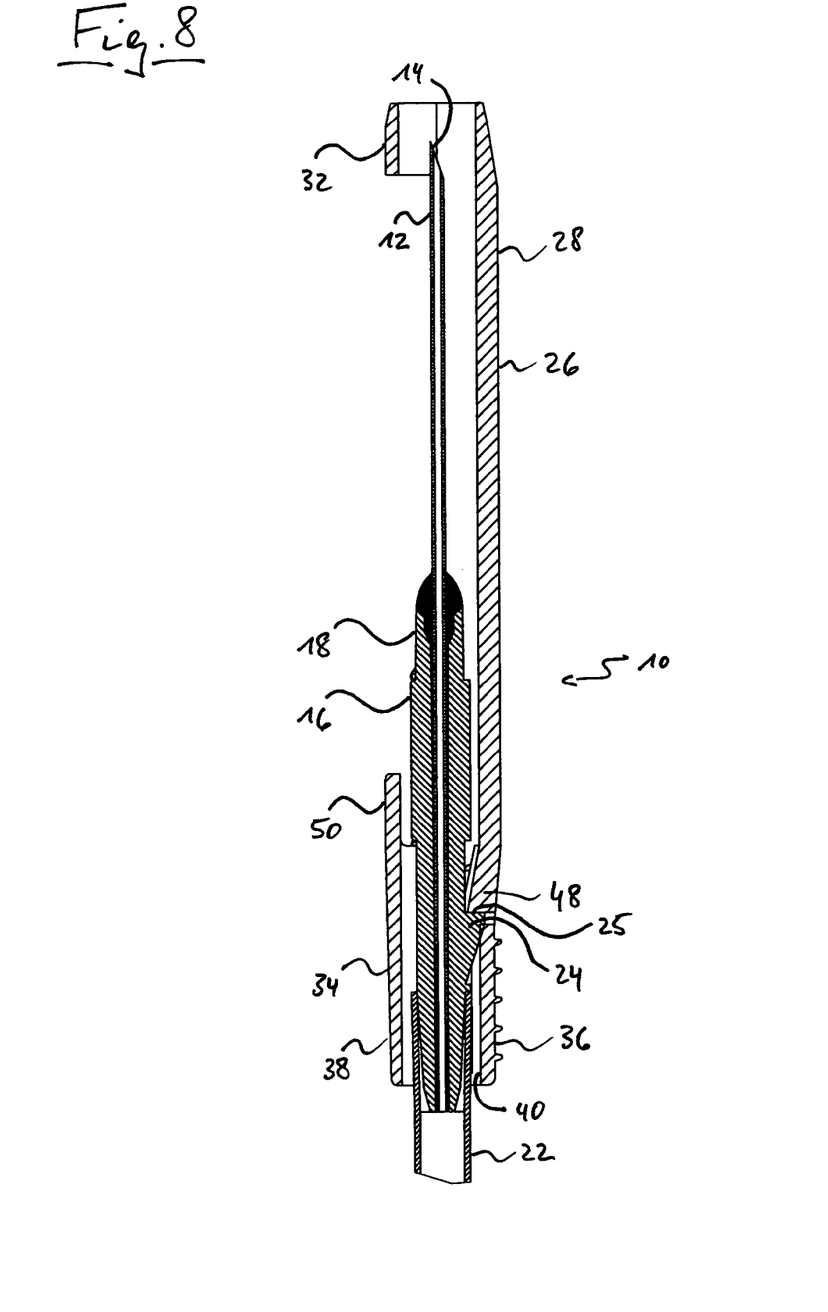
FIG. 8 is a cross-sectional view of the needle protector assembly of FIG. 1, taken along the axial direction of the assembly, with the needle received and locked in the protective cover.
Figure 9A:
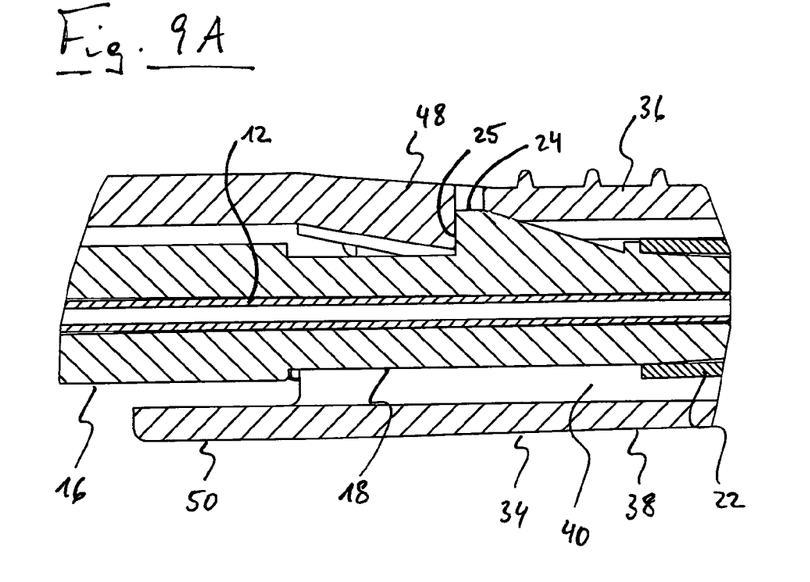
FIG. 9A is an enlarged section of the cross-sectional view of FIG. 8, showing in more detail the locking mechanism for the locking of the needle in the protective cover.
Figure 9B:
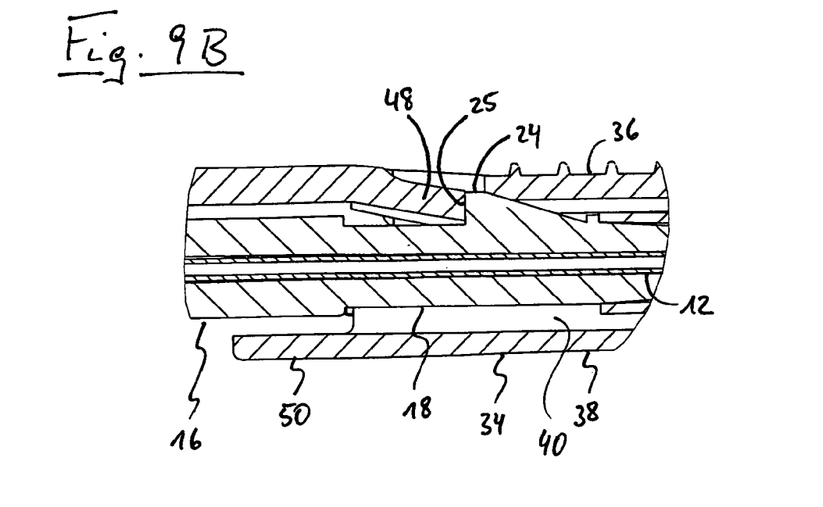
FIG. 9B is a cross-sectional view showing an alternative version of the locking mechanism.

Generally, the locking tongue 48 may have different shapes (FIGS. 9A and 9B). However, a compulsory requirement is that the locking tongue 48 needs to be shaped such that its free end abuts against the distal surface 25 of the locking protrusion 24 facing the needle tip 14 when the needle is fully received in the protective cover 26, as is shown in FIGS. 8, 9A and 9B.

A retaining element 50 is formed on the bottom part 38 of the flat portion 34. The retaining element 50 has the shape of a tongue-like extension which extends from a distal side of the bottom part 38 in the axial direction.

The function of the needle protector assembly 10 is as follows:

In the initial state of the needle protector assembly 10 the needle hub 16 is in a foremost distal position, herein referred to as the position of use, in which the wings 20 of the needle hub 16 are adjacent the tubular portion 32 of the protective cover and the needle 12 extends beyond the protective cover 32.

A medical professional holds the wings 20 attached to the needle hub 16 and punctures the skin of a patient with the needle 12 such that the needle 12 enters a vein of patient. As the needle 12 enters the vein blood rushes into the needle 12 and through the main body 18 of the needle hub 16 into the PVC tube 22. The blood is collected in a blood collection bag or a vacuum tube through a connection to the other end of the PVC tube 22. Alternatively, the device may be used to give fluids or medications to a patient.

After a required quantity of blood has been collected, the needle 12 is withdrawn from the vein by holding the wings 20. As the needle 12 is pulled out of the patient, it enters the protective cover 26. At the same time the wing housing moves backwards towards the flat portion 34 of the protective cover 26.

When the proximal end portion of the main body 18 of the wing housing has entered the internal passage 40 of the flat portion 34 of the protective cover 26, the locking protrusion 24 of the needle hub 16 engages with the locking tongue 48 of the protective cover 26. The locking tongue 48 runs up the sloped side of the locking protrusion 24 and is thereby pushed outward.

Once the needle hub 16 has adopted a position in which the needle 12 is fully received in the protective cover 26, herein referred to as the retracted position, the locking protrusion 24 has passed the locking tongue 48 such that the locking tongue 48 snaps back inside due to its resilient properties and engages behind the locking protrusion 24, thereby preventing movement of the needle hub 16 towards the distal end of the protective cover 26.

In the retracted position of the needle hub 16, the retaining element 50 extends over a portion of the bottom side of the needle hub 16. Thereby the retaining element 50 not only operates as a guide helping the needle hub 16 to correctly enter the internal passage 40 of the flat portion 34, but also prevents movement of the needle hub 16 in a radial direction away from the locking tongue 48 that could cause a disengagement of the locking protrusion 24 and the locking tongue 48, which could ultimately lead to the needle 12 accidentally coming out of the protective cover.

Hence, in the retracted position of the needle hub 16, the needle 12 is safely locked inside the protective cover 26 and the blood collection set can be safely disposed off without danger of the needle pricking any person.

FIGS. 13 to 18 show a needle protector assembly 110 according to a second embodiment, which may be used in a disposable medical device, such as a blood collection bag with needle. Elements corresponding to similar elements in the above described first embodiment will be denoted by the same reference numerals, increased by 100.

Figure 13:
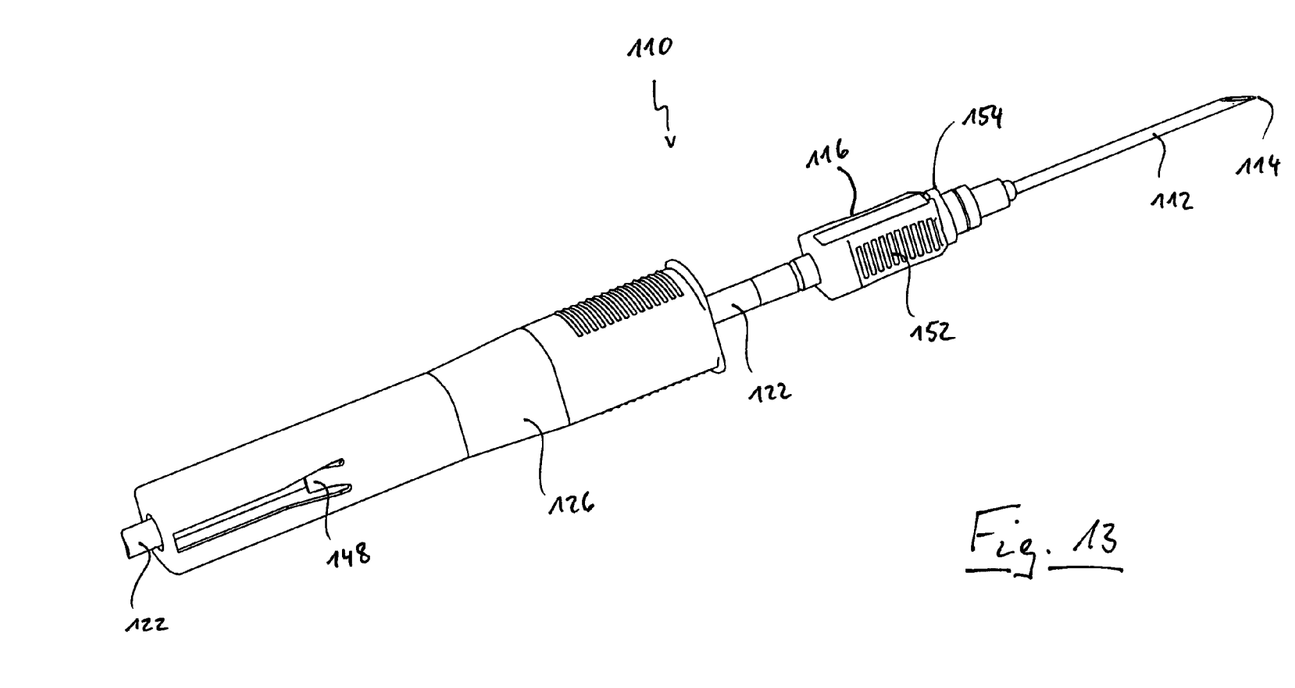
FIG. 13 is a perspective view of a needle protector assembly of the invention according to a second embodiment, wherein a needle protrudes beyond a protective cover.

The needle protector assembly 110 according to the second embodiment comprises a needle 112 having a needle tip 114 at its distal end. However, in contrast to the first embodiment, the needle 112 is not attached to a wing housing, but to a needle hub 116 which is generally shaped as a cuboid and which has slightly concave handling surfaces 152 on opposite side surfaces thereof.

Figure 16:
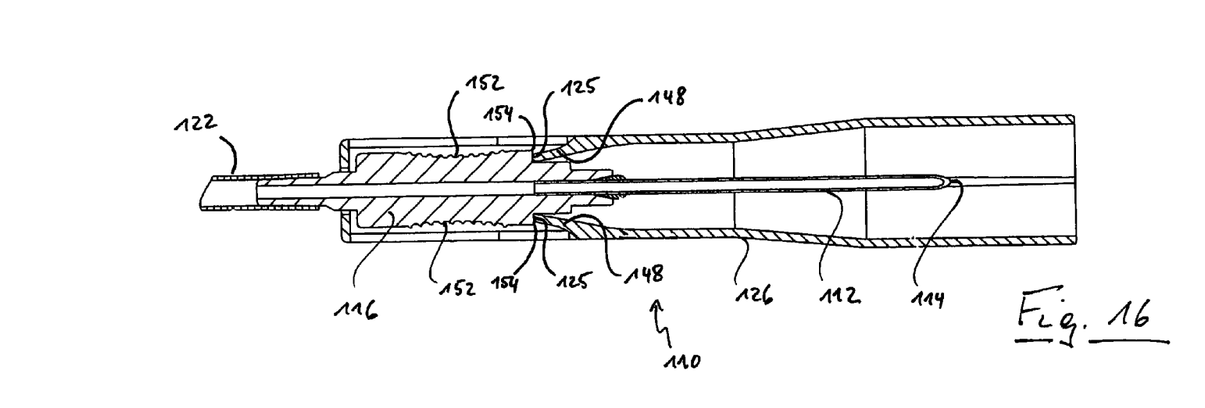
FIG. 16 is a cross-sectional view of the needle protector assembly of FIG. 13, taken along the axial direction of the assembly, with the needle received and locked in the protective cover.
Figure 17:
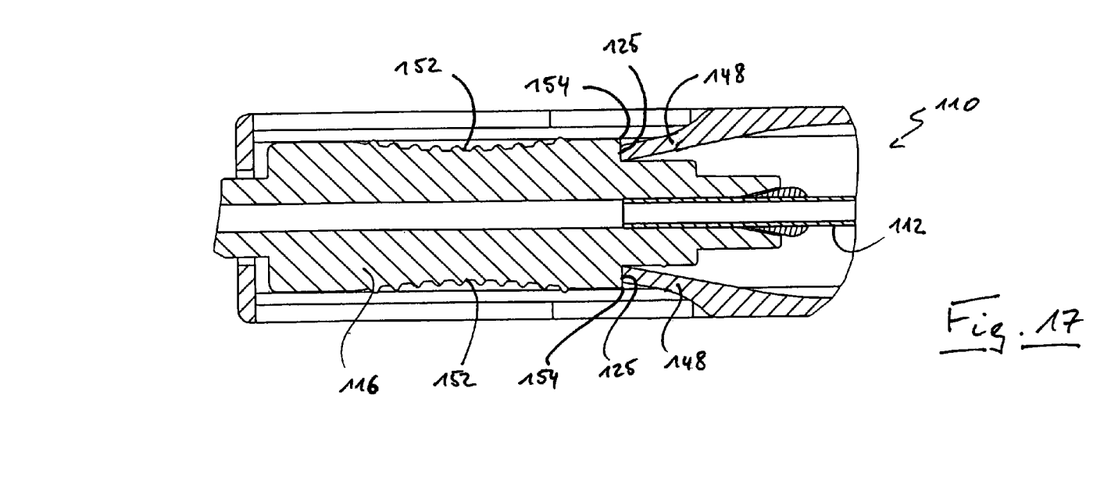
FIG. 17 is an enlarged section of the cross-sectional view of FIG. 16, showing in more detail the locking mechanism for the locking of the needle in the protective cover.

As is best seen in FIGS. 16 and 17, a shoulder 154 is formed on the needle hub 116, which defines a distal surface 125 facing the needle tip 114 and extending in a plane generally perpendicular to the axial direction of the needle 112.

At its proximal end, the needle hub 116 is connected to a PVC tube 122.

Figures 14A, 14B:
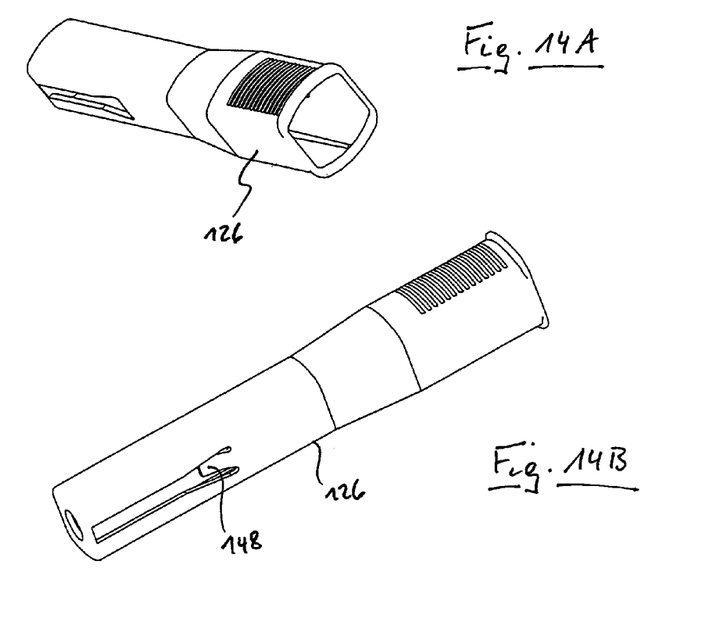
Figures 15A, 15B:
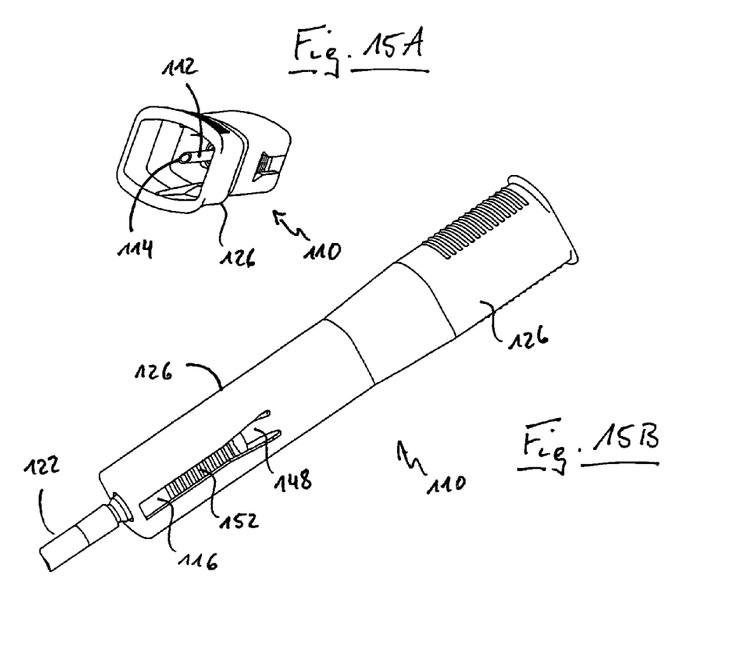

The needle protector assembly 110 further comprises a protective cover 126 which is tubular across its entire length as seen in the axial direction of the needle 114, when the needle hub 116 is received in the protective cover 126 (FIGS. 14 A to 15B).

Figure 18:
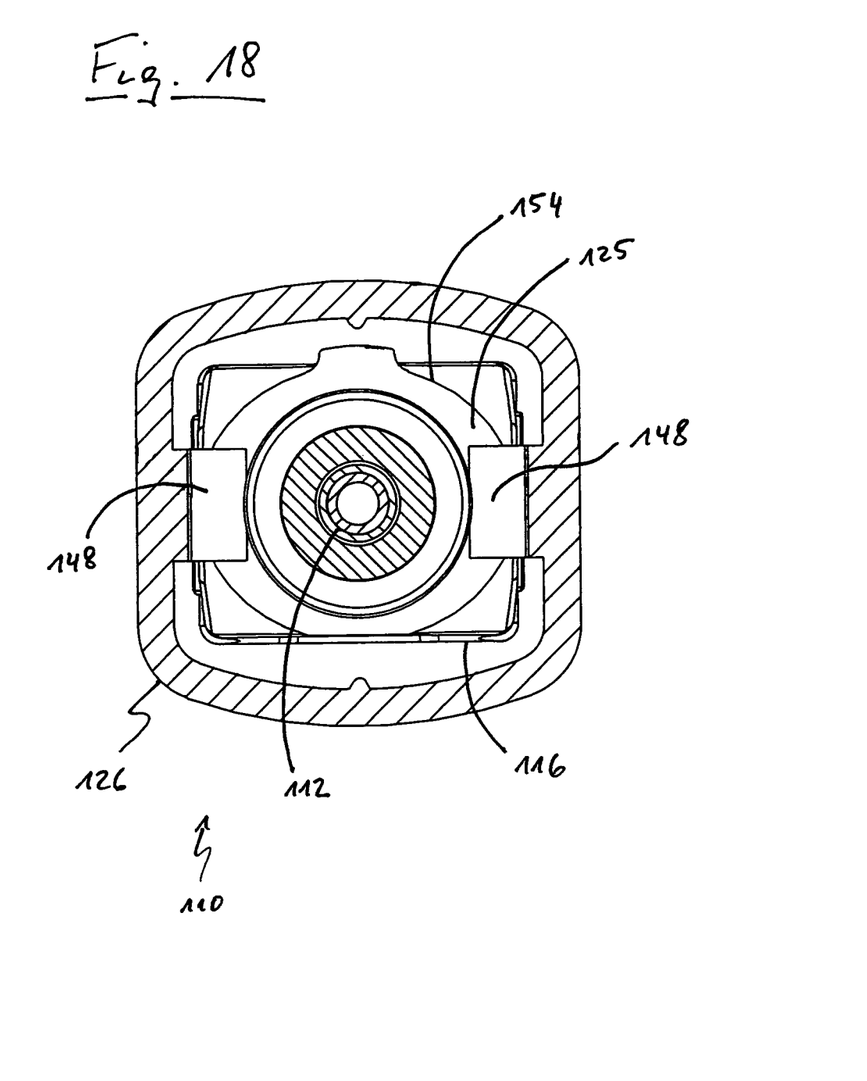
FIG. 18 is a cross-sectional view of the needle protector assembly of FIG. 13 in a plane perpendicular to the axial direction of the assembly, with the needle received and locked in the protective cover.

The protective cover 126 has a generally rectangular inner cross-section, seen in the plane perpendicular to the axial direction. The inner cross-section of the protective cover 126 is adapted to the outer cross-section of the needle hub 116, such that the needle hub 116 can enter the protective cover 126 and move inside the protective cover 126 towards the proximal end thereof.

In the region of the proximal end of the protective cover 126, two locking tongues 148 with spring-like properties are formed on opposite sides of the protective cover 126. The locking tongues 148 are integrally formed with the protective cover 126 and extend in the axial direction towards the proximal end of the protective cover 126. At the same time, the locking tongues 148 are bent inwards, i.e. they extend radially inwards into the internal cavity defined by the protective cover 126.

The function of the needle protector assembly 110 is as follows:

In the initial state of the needle protector assembly 110, the needle 112 and the needle hub 116 are outside of the protective cover 126 in a position of use. In this position the needle 112 can be inserted into a patient or a donor.

After the needle 112 has been withdrawn from the patient, the protective cover 126 is pushed over the needle hub 116 such that the needle hub 116 and the needle 112 enter the protective cover 126. By pulling on the PVC tube 122, the needle hub 116 is moved inside the protective cover 126 towards the proximal end thereof.

While the needle hub 116 moves towards the proximal end of the protective cover 126, the needle hub 116 engages with the locking tongues 148 and pushes the locking tongues 148 outwards against a restoring force of the locking tongues 148.

Once the needle hub 116 arrives in the region of the proximal end of the protective cover 126, the locking tongues 148 pass the distal shoulder 154 of the needle hub 116 and snap back inside the protective cover 126, thereby engaging behind the surface 125 of the needle hub 116.

In this situation the needle hub 116 has adopted a retracted position in which the needle 112 is fully received in the protective cover 126, and the needle 112 is securely locked inside the protective cover 126 by the locking tongues 148 preventing movement of the needle hub 116 in the axial direction towards the distal end of the protective cover. Thus the medical device can be safely disposed off without danger of the needle pricking any person.

Figure 19:
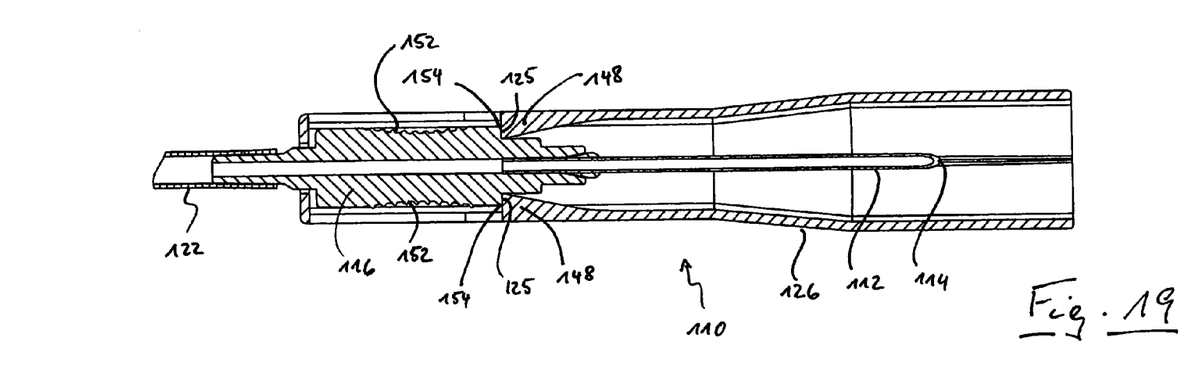
FIG. 19 is a cross-sectional view of a needle protector assembly of the invention according to a third embodiment, taken along the axial direction of the assembly, with the needle received and locked in the protective cover.
Figure 20:
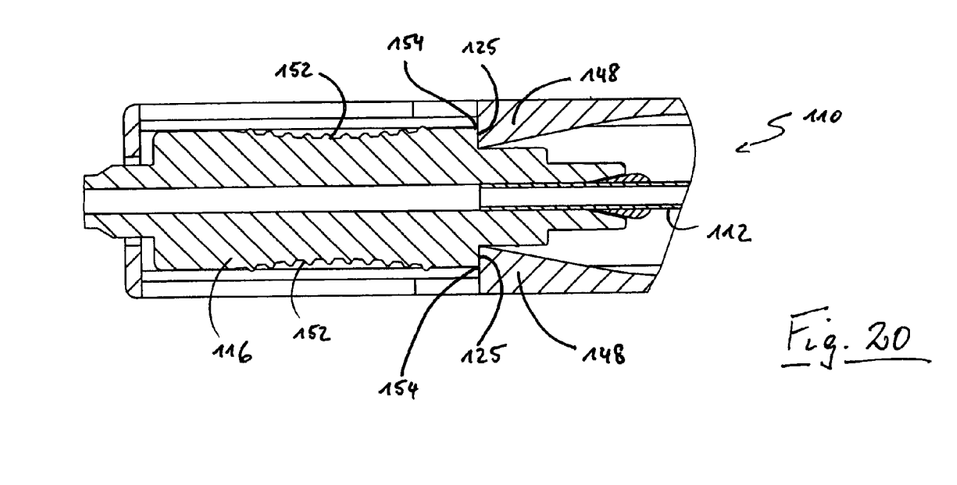
FIG. 20 is an enlarged section of the cross-sectional view of FIG. 19, showing in more detail the locking mechanism for the locking of the needle in the protective cover.

FIGS. 19 and 20 show a needle protector assembly 110 according to a third embodiment, which differs from the aforementioned described needle protector assembly 110 according to the second embodiment only in the shape of the locking tongues 148.

The locking tongues 148 of the third embodiment have a wedge-like profile with their outer surface being generally aligned with the outer surface of the protective cover 126 while the dimension of the locking tongues 148 in the radial direction increases towards the free ends of the locking tongues 148.

Alternative shapes of the locking tongues 148 are generally possible. However, a compulsory requirement is that the locking tongues 148 need to be shaped such that their free ends abut against the distal surface 125 of the shoulder 154 of the needle hub 116 when the needle 112 is fully received in the protective cover 126.

Furthermore, it is to be noted that embodiments of the needle protector assembly are possible in which the needle hub comprises both a shoulder which engages with one or more locking tongues of the protective cover and a protrusion which engages with either a locking tongue or an opening in the protective cover, when the needle hub is in the retracted position.

REFERENCE NUMERALS 10 needle protector assembly
12 needle
14 needle tip
16 needle hub
18 main body
20 wing
22 PVC tube
24 locking protrusion
25 distal surface
26 protective cover
28 elongate portion
30 guide rails
32 tubular portion
34 flat portion
36 top part
38 bottom part
40 passage
42 film hinge
44 latching mechanism
46 guide rails
48 locking tongue
50 retaining element
110 needle protector assembly
112 needle
114 needle tip
116 needle hub
118 main body
122 PVC tube
125 distal surface
126 protective cover
148 locking tongue
152 handling surface
154 shoulder

The invention claimed is:

1. A needle protector assembly comprising a needle and a protective cover for the needle,
wherein the needle is attached to a needle hub which can be moved relative to the protective cover between a position of use in which at least the tip of the needle is outside of the protective cover, and a retracted position in which the needle is fully received in the protective cover, the needle hub comprising a winged housing having a tubular main body and two wings which extend in opposite radial directions from the main body,
wherein the needle protector assembly further comprises a locking mechanism adapted to secure the needle hub inside the protective cover when the needle hub is in the retracted position,
wherein the locking mechanism comprises at least one pair of first and second locking means engaging with each other when the needle hub is in the retracted position, wherein the first locking means is provided on the needle hub and the second locking means is provided on the protective cover, and
wherein the first locking means:
has a generally nose-like or ramp-like shape, with a radial dimension increasing towards the tip of the needle,
is formed such that the radial dimension of the first locking means can be reduced against a restoring force, and
is arranged in the region of a proximal end of the needle hub;
wherein the locking mechanism comprises a retaining element securing the interlocking of the pair of first and second locking means;
wherein the retaining element is formed on a side of the needle protector assembly opposite from the pair of first and second locking means;
wherein the retaining element is an extension of the protective cover protruding from a proximal portion of the protective cover in a direction towards a distal end of the protective cover.

2. A needle protector assembly in accordance with claim 1, wherein at least two pairs of first and second locking means are arranged on the same side of the needle protector assembly and spaced apart from one another seen in the axial direction of the needle, when the needle hub is in the retracted position.

3. A needle protector assembly in accordance with claim 1, wherein at least one pair of first and second locking means is arranged on a first side of the needle protector assembly and at least one pair of first and second locking means is arranged on a second side of the needle protector assembly opposite from the first side, when the needle hub is in the retracted position.

4. A needle protector assembly in accordance with claim 1, wherein the first locking means is formed integrally with the needle hub.

5. A needle protector assembly in accordance with claim 1, wherein the first locking means defines a surface facing the needle tip, wherein at least a portion of the surface extends in a plane generally perpendicular to the needle.

6. A needle protector assembly in accordance with claim 1, wherein the first locking means comprises a protrusion protruding from the needle hub.

7. A needle protector assembly in accordance with claim 1, wherein the first locking means is formed from a material having elastic properties.

8. A needle protector assembly in accordance with claim 1, wherein the second locking means comprises an opening in the protective cover, which is adapted to receive the first locking means when the needle hub is in the retracted position.

9. A needle protector assembly in accordance with claim 1, wherein the second locking means comprises a locking tongue extending towards a proximal end of the protective cover and adapted to engage with the first locking means, when the needle hub is in the retracted position.

10. A needle protector assembly in accordance with claim 9, wherein the locking tongue has resilient properties and extends towards the interior of the protective cover such that the locking tongue is pushed outwards by the first locking means or by the needle hub as the needle hub is moved towards the refracted position, and snaps back behind the first locking means or the needle hub once the needle hub has adopted the retracted position.

11. A needle protector assembly in accordance with claim 9, wherein the locking tongue is integrally formed with the protective cover.

12. A needle protector assembly in accordance with claim 1, wherein the protective cover comprises guiding means for guiding the first locking means into engagement with the second locking means when the needle hub is moved towards the retracted position.

13. A needle protector assembly in accordance with claim 1, wherein the protective cover comprises an elongate portion having the shape of one half of a tube cut at least approximately in half in the axial direction.

14. A needle protector assembly in accordance with claim 1, wherein the protective cover comprises a tubular portion in the region of a distal end of the protective cover.

15. A needle protector assembly in accordance with claim 1, wherein the protective cover comprises a flat portion in the region of a proximal end of the protective cover.

16. A needle protector assembly in accordance with claim 15, wherein the flat portion comprises first and second parts defining an internal passage in which the needle hub is received when the needle hub is in the retracted position.

17. A needle protector assembly in accordance with claim 16, wherein the first and second parts are integrally formed and connected to one another by a film hinge.

18. A needle protector assembly in accordance with claim 16, wherein the first and second parts are attached to each other by means of at least one of a latching mechanism, an adhesive and welding.

19. A needle protector assembly comprising a needle and a protective cover for the needle,
wherein the needle is attached to a needle hub which can be moved relative to the protective cover between a position of use in which at least the tip of the needle is outside of the protective cover, and a retracted position in which the needle is fully received in the protective cover, the needle hub comprising a winged housing having a tubular main body and two wings which extend in opposite radial directions from the main body,
wherein the needle protector assembly further comprises a locking mechanism adapted to secure the needle hub inside the protective cover when the needle hub is in the retracted position,
wherein the locking mechanism comprises at least one pair of first and second locking means engaging with each other when the needle hub is in the retracted position, wherein the first locking means is provided on the needle hub and the second locking means is provided on the protective cover, and
wherein the first locking means:
has a generally nose-like or ramp-like shape, with a radial dimension increasing towards the tip of the needle,
is formed such that the radial dimension of the first locking means can be reduced against a restoring force, and
is arranged in the region of a proximal end of the needle hub,
wherein the first locking means is formed on a ring attached to the needle hub.

\* \* \* \* \*